(12) United States Patent
Freund

(10) Patent No.: US 9,138,371 B2
(45) Date of Patent: Sep. 22, 2015

(54) THERAPEUTIC GARMENT, APPARATUS, METHOD, AND SYSTEM HAVING INFLATABLE BLADDERS

(75) Inventor: Robert M. Freund, Old Westbury, NY (US)

(73) Assignee: Angiosome, Inc., Greenwich, CT (US)

( * ) Notice: Subject to any disclaimer, the term of this patent is extended or adjusted under 35 U.S.C. 154(b) by 716 days.

(21) Appl. No.: 13/282,170

(22) Filed: Oct. 26, 2011

(65) Prior Publication Data

US 2013/0035619 A1 Feb. 7, 2013

Related U.S. Application Data

(60) Provisional application No. 61/515,774, filed on Aug. 5, 2011.

(51) Int. Cl.
*A61H 7/00* (2006.01)
*A61H 9/00* (2006.01)
(Continued)

(52) U.S. Cl.
CPC .......... *A61H 9/0078* (2013.01); *A41D 13/1245* (2013.01); *A61B 5/01* (2013.01); *A61B 5/447* (2013.01); *A61B 5/6804* (2013.01); *A61B 2562/029* (2013.01); *A61G 7/05769* (2013.01); *A61G 2007/05784* (2013.01); *A61G 2203/34* (2013.01); *A61G 2203/46* (2013.01); *A61H 23/02* (2013.01); *A61H 23/0245* (2013.01); *A61H 2201/0184* (2013.01); *A61H 2201/0214* (2013.01); *A61H 2201/1614* (2013.01);
(Continued)

(58) Field of Classification Search
CPC ....... A61H 9/00; A61H 9/0078; A61H 23/00; A61H 23/02; A61H 23/0245; A61H 2201/0214; A61H 2201/1614; A61H 2201/1623; A61H 2201/5002; A61H 2201/5058; A61H 2201/5071; A61H 2201/5082; A61H 2201/5097; A61H 2201/0184; A61H 2203/0456; A61H 2230/00; A61G 2007/05784; A61G 2003/34
USPC ............ 601/2, 15, 46, 55, 56, 57, 75, 84, 88, 601/96, 105, 107, 108, 134, 148–152; 602/13; 606/201, 202, 203; 128/DIG. 20; 2/69, DIG. 3; 5/710, 713, 5/715
See application file for complete search history.

(56) References Cited

U.S. PATENT DOCUMENTS 4,416,664 A 11/1983 Womack
5,003,654 A 4/1991 Vrzalik
(Continued)

FOREIGN PATENT DOCUMENTS

BR P10701887-8 A2 1/2009

OTHER PUBLICATIONS

PCT Search Report, Patent Cooperation Treaty, Oct. 1, 2012.

*Primary Examiner* — Quang D Thanh
(74) *Attorney, Agent, or Firm* — Keith D. Nowak; Carter Ledyard & Milburn LLP

(57) ABSTRACT

A therapeutic garment includes at least one first expandable bladder configured to underlie a wearer's left shoulder blade, at least one second expandable bladder configured to underlie the wearer's right shoulder blade, and an actuator configured to alternatingly (a) expand the at least one first expandable bladder from a collapsed state to an expanded state such that the wearer's torso is rolled in a rightward direction and (b) expand the at least one second expandable bladder from a collapsed state to an expanded state such that the wearer's torso is rolled in a leftward direction.

15 Claims, 5 Drawing Sheets

(51) Int. Cl.
  *A41D 13/12* (2006.01)
  *A61B 5/01* (2006.01)
  *A61H 23/02* (2006.01)
  *A61B 5/00* (2006.01)
  *A61G 7/057* (2006.01)

(52) U.S. Cl.
  CPC . *A61H2201/1623* (2013.01); *A61H 2201/1652* (2013.01); *A61H 2201/5002* (2013.01); *A61H 2201/5058* (2013.01); *A61H 2201/5071* (2013.01); *A61H 2201/5082* (2013.01); *A61H 2201/5097* (2013.01); *A61H 2203/0456* (2013.01); *A61H 2230/00* (2013.01)

(56) References Cited

U.S. PATENT DOCUMENTS

| | | |
|---|---|---|
| 6,171,270 B1 * | 1/2001 | Gau .............................. 601/150 |
| 6,179,793 B1 | 1/2001 | Rothman et al. |
| 7,771,376 B2 | 8/2010 | Roth et al. |
| 2004/0097854 A1 * | 5/2004 | Hester et al. ................... 601/149 |
| 2005/0126578 A1 | 6/2005 | Garrison et al. |
| 2007/0088239 A1 * | 4/2007 | Roth et al. ..................... 601/152 |
| 2010/0179586 A1 * | 7/2010 | Ward et al. .................... 606/202 |

* cited by examiner

THERAPEUTIC GARMENT, APPARATUS, METHOD, AND SYSTEM HAVING INFLATABLE BLADDERS

CROSS-REFERENCE TO RELATED APPLICATIONS

This application claims the benefit of U.S. Provisional Patent Application No. 61/515,774, filed on Aug. 5, 2011, which is expressly incorporated herein in its entirety by reference thereto.

FIELD OF THE INVENTION

The present invention relates to a therapeutic garment, apparatus, method, and system having inflatable bladders.

BACKGROUND OF THE INVENTION

U.S. Pat. No. 7,823,219 ("the '219 patent"), which issued on Nov. 2, 2010 and which is incorporated herein in its entirety by reference thereto, describes a therapeutic pressure-relieving device and method for preventing and treating pressure sores (i.e., decubitus ulcers) on a patient's body. The device of the '219 patent is intended to prevent and treat pressure sores by alleviating pressure on tissue covering and surrounding bony prominences of the patient's body and by alleviating pressure on the blood vessels in the angiosomes to promote blood flow. The device of the '219 patent uses a plurality of inflatable channels or pockets which are selectably inflatable to alleviate pressure while allowing blood to flow throughout the angiosomes.

Although the device of the '219 patent is configured to alleviate pressure sores in particular regions of the patient's body, it is also desirable to roll the patient's body, as described in further detail below.

Pressure sores may be considered a function of pressure that is exerted on a soft tissue surface of the body greater than 32 mm Hg for a substantial period of time. One way to minimize or at least reduce this problem is to manually roll the patient from side to side at a relatively high frequency. This is sometimes referred to as "log rolling." Problems with this treatment include increased nursing requirements, delays between rolling treatments, and sheer forces on the skin during the "rolling" procedure. Also, abrupt and relatively rapid rolling may tend to cause discomfort to the patient.

Accordingly, there is believed to be a need for a device and method that provides the benefits of rolling the patient while reducing manual labor requirements, trauma to the patient's tissue, and patient discomfort associated with such rolling.

Further, especially for hospitalized, bed-ridden patients, pulmonary function may be reduced from normal levels for various reasons. A factor in pulmonary disease occurrence is the inability to clear fluid build-up in the lungs. As the fluid accumulates, the risk of pneumonia and pulmonary desaturation may increase. Thus, there is a need for a device and method for facilitating pulmonary function, especially for bed-ridden patients.

There is also believed to be a need to apply automatically percussive treatment to break up inspissated fluids within the patient's lungs, reducing surface tension, so as to allow secretions to be mobilized and expectorated, while reducing the need for nurses and pulmonary therapists to provide such treatment.

Especially for a closed garment, such as, for example, the device of the '219 patent, a limiting feature in a debilitated patient may include the risk of undiagnosed fecal or urinary soilage. This soilage may result in skin breakdown, wound infection, and/or patient discomfort. If the garment is closed, nurses may have a limited opportunity to examine the patient. Accordingly, there is believed to be a need for detection devices and methods for detecting urinary and fecal soilage and alerting nurses to these occurrences, so as to inform or signal the nurses to perform a garment change, so as to reduce the amount of time spent by the nurses checking on soilage of patients.

Furthermore, many patients may undergo cardiac catheterization and other invasive procedures that may require access from the large blood vessels (such as, for example, the groin area). After these procedures are completed, catheters are removed and the puncture wound in the blood vessels may bleed for hours. To circumvent this bleeding, a nurse places pressure on the blood vessels or places a "brick" or "sandbag" on the area (for example, for up to one hour). Each of these solutions is complicated by patient discomfort and the risk of bleeding if the pressure brick/bag shifts so that it no longer properly puts pressure on the blood vessel.

Thus, there is believed to be a need for an apparatus and method that effectively applies pressure during invasive procedures (for example, catheterization procedures), without relying upon manually applied pressure and/or the placement of a weight on the patient's body in the area where the bleeding occurs. In this regard, there is believed to be a need for devices and methods that minimize bleeding, conform to the patient's anatomy, and/or have an integrated bleeding alarm to alert a nurse if bleeding occurs.

To further facilitate prevention of pressure sores and improve patient comfort, there is also believed to be a need for an apparatus and method for distributing a gas to a patient's skin to reduce moisture and perspiration.

SUMMARY OF THE INVENTION

Example embodiments of the present invention may be used in combination with or separate and apart from the device and method of the '219 patent.

In accordance with example embodiments and/or methods of the present invention, a therapeutic garment includes: at least one first expandable bladder configured to underlie a wearer's left shoulder blade; at least one second expandable bladder configured to underlie the wearer's right shoulder blade; and an actuator configured to alternatingly (a) expand the at least one first expandable bladder from a collapsed state to an expanded state such that the wearer's torso is rolled in a rightward direction and (b) expand the at least one second expandable bladder from a collapsed state to an expanded state such that the wearer's torso is rolled in a leftward direction.

In accordance with the example embodiments and/or methods of the present invention, the at least one first expandable bladder may be elongated with a longitudinal axis parallel to the wearer's anteroposterior axis, and the at least one second expandable bladder may be elongated with a longitudinal axis parallel to the wearer's anteroposterior axis.

In accordance with the example embodiments and/or methods of the present invention, the rate of the alternating rolling may be adjustable.

In accordance with the example embodiments and/or methods of the present invention, the garment may include at least one percussive mechanism to transmit at least one of (a) ultrasonic waves and (b) a direct percussive effect, to the wearer's lungs.

In accordance with the example embodiments and/or methods of the present invention, at least one percussive mechanism may be disposed in the at least one first expandable bladder and the at least one second bladder.

In accordance with the example embodiments and/or methods of the present invention, the garment may include at least one vibratory mechanism configured to transmit vibrations to the wearer's lungs.

In accordance with the example embodiments and/or methods of the present invention, the at least one vibratory mechanism may be disposed in the at least one first expandable bladder and the at least one second expandable bladder.

In accordance with the example embodiments and/or methods of the present invention, the garment may include at least one control panel to set at least one of (a) an intensity of treatment, (b) a duration of treatment, and (c) a frequency of treatment.

In accordance with the example embodiments and/or methods of the present invention, the garment may include at least one sensor to detect at least one of (a) urinary soilage and (b) fecal soilage.

In accordance with the example embodiments and/or methods of the present invention, the garment may include an alarm that is configured to be triggered by the at least one sensor upon the detection of at least one of (a) urinary soilage and (b) fecal soilage.

In accordance with the example embodiments and/or methods of the present invention, the garment may include at least one third expandable bladder configured to exert a pressure on a vascular access of the wearer that is sufficient to reduce bleeding from the vascular access.

In accordance with example embodiments and/or methods of the present invention, a method for reducing bleeding in connection with an invasive procedure conducted on a patient includes: disposing at least one expandable bladder adjacent a vascular access of the patient; and expanding the at least one expandable bladder to exert a pressure onto the patient's tissue sufficient to minimize bleeding from the vascular access.

In accordance with example embodiments and/or methods of the present invention, a method for rolling a patient includes: providing at least one first expandable bladder below the patient's left shoulder blade; providing at least one second expandable bladder below the patient's right shoulder blade; and alternatingly expanding and collapsing the at least one first expandable bladder and the at least one second expandable bladder so that the wearer's torso is alternately rolled in a rightward direction and a leftward direction.

In accordance with example embodiments and/or methods of the present invention, a therapeutic apparatus is provided as a garment with two or more expandable bladders (or "pontoons"), which are configured to extend under each of the patient's shoulder blades. The expandable bladders are configured to inflate and deflate in an alternating pattern to so as to roll the patient side-to-side in correspondingly alternating directions. This side-to-side rolling is intended to prevent and/or reduce pressure sores, as well as improve pulmonary hygiene (i.e., pulmonary toilet).

Example embodiments and/or methods of the present invention include an apparatus, system, and method for rolling the patient, with the expandable bladders, side-to-side in a motion sequence. As the patient rolls side-to-side in a "rolling" process, the risks of pressure sores, which may already be diminished by the garment, are believed to be reduced further. The slow rolling apparatus and method is also believed to be more comfortable for the patient than an abrupt rolling side-to-side to the other by nurses, who may be rushed to perform this maneuver in an expedient manner (such as, for example, due to time pressure). The expandable bladder system is also intended to reduce the amount of nursing care required by eliminating the labor intensive manual rolling procedure.

In accordance with the example embodiments and/or methods of the present invention, the "rolling" is also intended to improve pulmonary function by shifting the position of the patient, so as to liberate fluid secretions that have accumulated within the patient's lungs and help at least reduce the risk of pneumonia.

In accordance with example embodiments and/or methods of the present invention, multiple expandable bladder systems (for example, two to six expandable bladders) are oriented vertically, i.e., along or parallel to the patient's anteroposterior axis, as part of a pressure-sore-reducing garment. The expandable bladders may extend the vertical length of the garment and/or may extend up to the top of the shoulders. The expandable bladders are configured to inflate and deflate in a manner so that the patient gently rolls back and forth. The rate and/or frequency of rolling may be adjusted, for example, with the pump mechanism.

In accordance with example embodiments and/or methods of the present invention, to enhance the pulmonary hygiene function, percussive mechanisms may be included or integrated with the expandable bladders to create a percussive effect to help mobilize sequestered secretions within the lungs of debilitated and/or bed-ridden patients. Such percussive treatments are intended to break up inspissated fluids within the lungs and reduce surface tension, so as to allow secretions to be mobilized and expectorated. Such devices and methods are intended to reduce the need for nurses and pulmonary therapists to provide manual percussive treatments. Also, because the treatment mechanism is included or integrated with the garment, percussive therapy may be increased in frequency since it may be controlled in an automated manner.

In accordance with the example embodiments and/or methods of the present invention, the percussive mechanisms may be provided, for example, within the pontoons, as a mechanical device that imparts percussive waves in the form of ultrasonic waves and/or direct percussion onto the patient's back, so as to transmit the percussive waves into the patient's lungs. The device may have one or more control panels that determine the intensity, duration and/or frequency of treatment.

In accordance with the example embodiments and/or methods of the present invention, the therapeutic apparatus may include sensors for urinary and/or fecal soilage, which are configured to alert nurses to the occurrence of urinary and/or fecal soilage, and for signaling the nurses to perform a garment change. The sensors may also allow nurses to spend less time checking patients for urinary and fecal soilage.

In accordance with the example embodiments and/or methods of the present invention, the sensors may be integrated into the garment and may be associated with an alarm disposed, for example, within the pump mechanism.

In accordance with example embodiments and/or methods of the present invention, a vascular compression garment, for post-vascular access patients, includes pressure bladders that provide only enough pressure to minimize or at least reduce bleeding in connection with invasive procedures (such as, for example, cardiac catheterizations). The pressure bladders may conform to the patient's body and/or have an integrated bleeding alarm to alert nurses if bleeding occurs. The garment may be integrated with the therapeutic garment described above or provided as a separate and stand-alone apparatus.

In accordance with the example embodiments and/or methods of the present invention, the garment may be included or integrated with a larger garment that limits shifting so that pressure is only placed where it is anatomically needed. This larger garment may be, for example, the therapeutic apparatus as described above.

In accordance with example embodiments of the present invention, an expandable bladder system includes an expandable bladder having a semi-permeable material to allow a gas, such as air, to pass across the semi-permeable membrane to reduce skin moisture and perspiration of a patient.

Further features and aspects of example embodiments and/or methods of the present invention are described in more detail below with reference to the appended Figures. Additional specific embodiments, aspects and advantages of the present invention are not restricted by the exemplary embodiments of the present invention.

DETAILED DESCRIPTION

Figure 1:
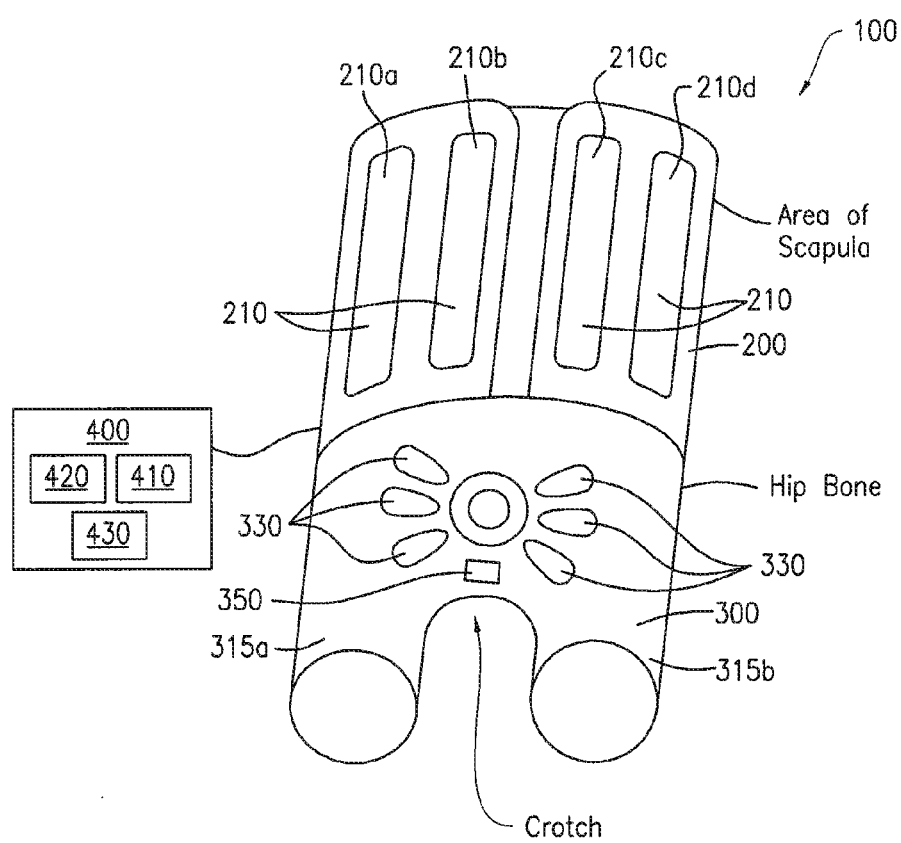
FIG. 1 shows a posterior view of an apparatus in accordance with an example embodiment of the present invention.

As to the figures, like reference characters indicate corresponding or like parts throughout the several figures.

Figure 2:
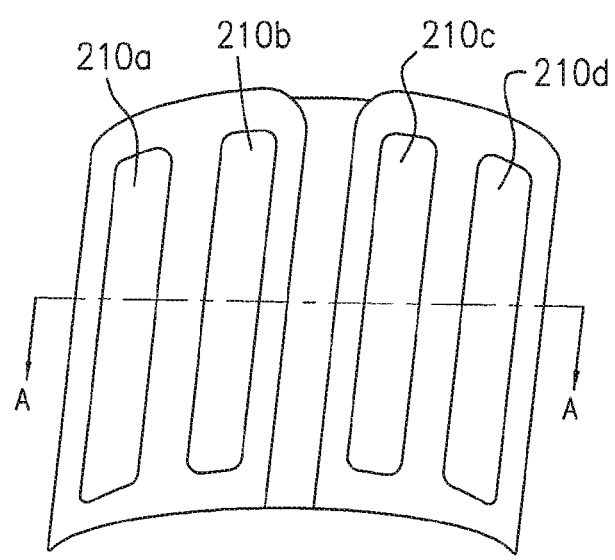
FIG. 2 shows a posterior partial view of the apparatus of FIG. 1.
Figure 3:
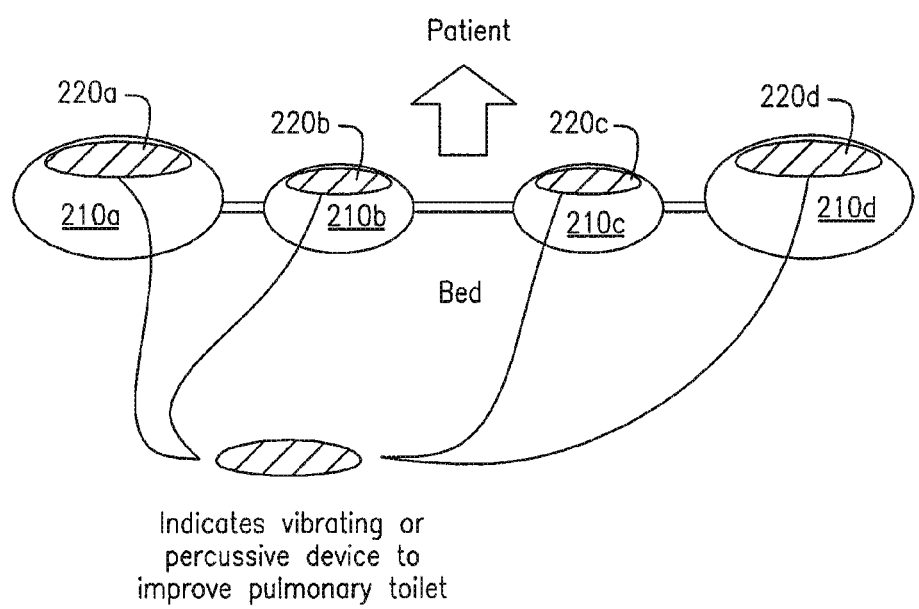
FIG. 3 shows a cross-sectional view corresponding to section A-A of FIG. 2.

FIGS. 1 to 3 show a therapeutic apparatus in the form of a garment 100. The garment 100 includes a torso section 200 connected to a pelvic section 300 having leg portions 315a and 315b adjacent a crotch region and configured to receive the patient's left and right legs respectively. The torso section 200 includes a plurality of elongated expandable bladders 210, which, when the garment 100 is worn by a patient, longitudinally extend vertically or parallel to the anteroposterior axis of the patient. In the system of FIG. 1, the garment 100 includes four expandable bladders 210a, 210b, 210c, 210d, with a first pair 210a, 210b configured to underlie the patient's left scapula and a second pair 210c, 210d configured to underlie the patient's right scapula. It should be understood, however, that any suitable number of bladders 210, including a single bladder 210, may be provided under each of the left scapula and the right scapula.

A control unit 400 includes a pump mechanism 420 controlled by a processor 410 to selectably expand the bladders 210a, 210b, 210c, 210d. The pump mechanism 420 may be, for example, the same as or like the pump described in the '219 patent, which is described in greater detail above and which is incorporated by reference in its entirety by reference thereto. The control unit 400 is configured to control the expansion of each bladder 210a, 210b, 210c, 210d independently to provide a highly controllable level of localized force at the location of each bladder 210a, 210b, 210c, 210d.

The processor 410 is programmed to expand bladders 210a and 210b while the bladders 210c and 210d are in a relatively deflated or non-expanded state, thus providing a rolling force that lifts the patient's back, in the area of the left scapula, to rotate the patient's torso rightward. Subsequently, the bladders 210a and 210b are deflated and the bladders 210c and 210d are expanded, so as to rotate the patient's torso leftward in an analogous manner. This process is repeated for any desired number of iterations or "rolls," which may be predetermined and/or provided to the control unit 400 by an operator and/or the patient. Further, the rate of rolling and any amount of time between commencements of rolling treatment sessions (for example, every 10 to 20 minutes) may be predetermined and/or adjusted, for example, by the operator and/or patient.

FIG. 1 shows that the garment 100 is integrated with components as described in the '219 patent, which is discussed in greater detail above and which is incorporated herein in its entirety by reference thereto. For example, the garment 100 includes channels 335 and pressure relievers 346, as described in the '219 patent. These elements may be controlled, along with the bladders 400 and/or any other controllable components described herein, by the control unit 400 and/or a separate controller.

FIG. 1 also shows that the garment 100 includes a soilage sensor 350 that is disposed in the groin region of the garment and that is configured to detect urinary and/or fecal soilage to alert, e.g., nurses, to the occurrence of urinary and/or fecal soilage. This signals the nurse to perform a garment change. The sensor may also allow the nurse to spend less time checking a patient for urinary and for fecal soilage. Although a single sensor 350 is shown, any number of sensors may be provided, as appropriate. The illustrated sensor is integrated into the garment and is associated with an alarm 450 disposed within the control unit 400. The alarm may be provided at any suitable location, and it may be configured to receive signals using wired and/or wireless communication.

Referring to FIG. 3, since the patient's back is generally angled with respect to the surface (e.g., the bed), supporting the patient's back during the respective right and left rolling movements, the outer bladders 210a and 210d hold a larger volume of pressurization fluid, or at least have a geometry that allows the bladders 210a and 210d to extend a greater distance between the patient's back and the surface on which the patient is lying.

The control unit 400 may be integrated into the garment or provided as a separate unit, such as, for example, a hand-held device. Further, the processor 410 and the pump mechanism 420 may be provided in the same housing or separate housings and may communicate with each other through wired and/or wireless communication channels.

The pump mechanism includes one or more pumps that are controllable to selectably pressurize and expand the bladders 210a, 210b, 210c, 210d via a pressurization fluid (e.g., a gas or liquid) that extends through pressure control lines and into the interior chambers of the bladders 210a, 210b, 210c, 210d.

In FIG. 3, each of the bladders 210a, 210b, 210c, 210d includes a respective vibrating and/or percussive device 220a, 220b, 220c, 220d disposed on the side of the respective bladder 210a, 210b, 210c, 210d adjacent the patient's back so as to improve pulmonary hygiene. The devices 220a, 220b, 220c, 220d create a vibratory and/or percussive effect to help mobilize sequestered secretions within the lungs of, e.g., debilitated and/or bed-ridden patients. Such vibratory and/or percussive treatments are intended to break up inspissated fluids within the lungs, reducing surface tension, so as to allow secretions to be mobilized and expectorated. This is intended to reduce the need for a nurse and for a pulmonary therapist to provide percussive treatment. Also, because the treatment mechanism is integrated into the garment, percussive therapy may be increased in frequency since it may be controlled in an automated manner. The vibrating and/or percussive devices 220a, 220b, 220c, 220d may be controlled, such as, for example, independently of each other, by the control unit 400 and/or a separate controller.

Although the vibrating and percussive devices 220*a*, 220*b*, 220*c*, 220*d* are integrated into the bladders 210*a*, 210*b*, 210*c*, 210*d*, the vibrating and/or percussive devices 220*a*, 220*b*, 220*c*, 220*d* may be provided separate from the bladders 210. Further, multiple vibrating and/or percussive devices may be provided for each bladder 210*a*, 210*b*, 210*c*, and/or 210*d*.

The vibrating and/or percussive devices 220*a*, 220*b*, 220*c*, 220*d* may apply mechanical percussion (for example, a cupping mechanism or paddle paddles that rotate back-and-forth) and/or ultrasonic vibration, which is intended to increase the effect of pulmonary surfactants. The vibrating and/or percussive devices 220*a*, 220*b*, 220*c*, 220*d* may be controlled (for example, by the controller 400) to provide vibration and/or percussion to the patients lungs simultaneously with the side-to-side "rolling" provided by the actuation of the bladders 210*a*, 210*b*, 210*c*, 210*d*.

Although "rolling" and vibration/percussion may be advantageous when applied alone or separately, it is believed that the simultaneously operable combination of a vibration/percussion mechanism and a "rolling" mechanism enhances the pulmonary benefits to the patient as compared to the application of these treatments applied alone or separately.

Figure 4:
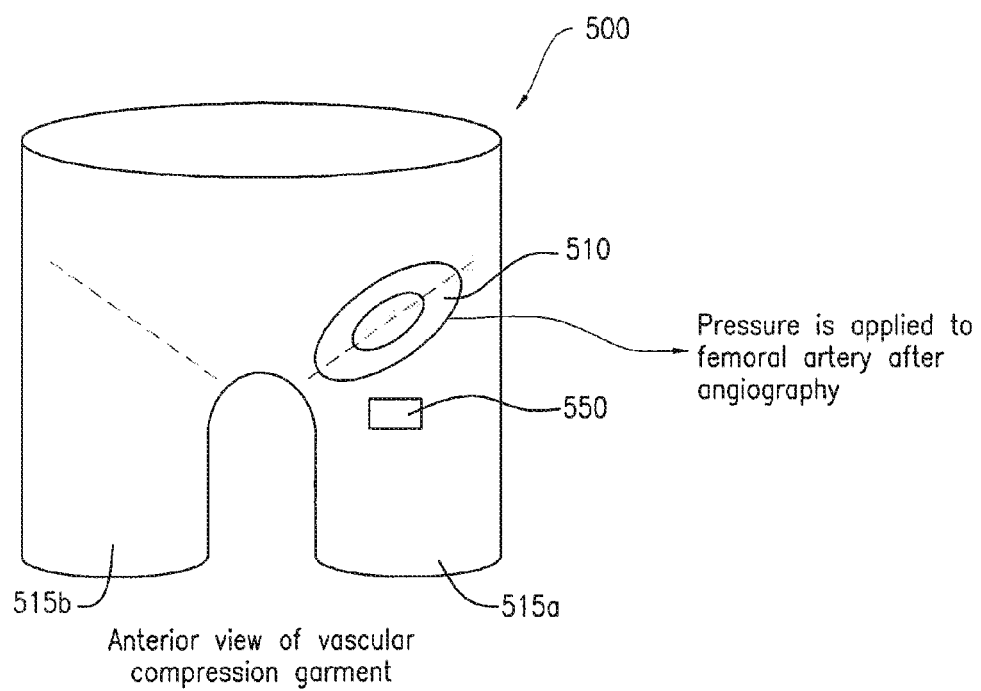
FIG. 4 shows an anterior view of a vascular compression garment in accordance with an example embodiment of the present invention.

Referring to FIG. 4, a vascular compression garment 500 is configured to be worn to surround around a patient's hip and upper thigh region in a manner similar to compression shorts. The garment 500 includes leg portions 515*a* and 515*b* configured to receive a patient's left and right legs, respectively.

An expandable vascular compression bladder 510 is provided in the region of a vascular access and is controllable (for example, with controller 400 or a separate controller) in a manner like that of the control and pressurization of the bladders 210, as described above. Although the bladder 510 is a single oval-shaped bladder, any number of bladders may be provided, and they may be separately controllable for applying pressure to the femoral artery.

The garment 500 is configured to provide only enough pressure to minimize or at least reduce bleeding in connection with an invasive procedure, such as, for example, cardiac catheterization. The pressure bladder conforms to the patient's body and includes an integrated bleeding sensor 550 that triggers an alarm to alert nurses if bleeding occurs. The alarm mechanism may function in connection with a control unit (e.g., control unit 400), in a manner like that of the soilage sensor 350, as described above.

In response to the triggering of the alarm by the bleeding sensor 550, a nurse may conduct manual intervention (including, for example, a visual inspection for bleeding) and/or the device may be controlled (for example, automatically) to increase the pressure applied to the vascular access region with the bladder 510.

The garment 500 may be integrated with the therapeutic garment 100 described above or provided as a separate and stand-alone apparatus.

Furthermore, the garment 500 may be integrated into a larger garment that limits shifting so that pressure is only placed where it is anatomically needed. This larger garment may be, e.g., the therapeutic garment 100, as described above.

Further, although the garment 500 is configured to apply pressure to the femoral artery (for example, after an angiography procedure), the garment 500 may be configured to apply pressure to any appropriate access location in connection with any suitable procedure.

Figure 5:
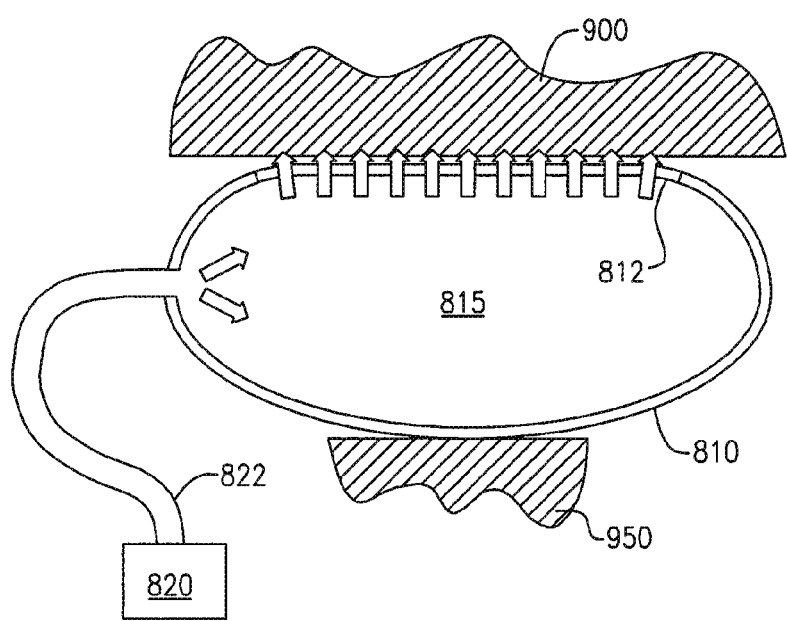
FIG. 5 shows a cross-sectional view of an expandable bladder system in accordance with an example embodiment of the present invention.

FIG. 5 shows a system that includes a semi-permeable material 812 in the region of an expandable bladder 815 that is in approximation with a patient 900 supported on a bed 950.

A pump 820 (which may be the same as pump 420 shown in FIG. 1) is controlled to supply air (or any other suitable gas), via supply line 822, to the interior space 815 of the bladder 815. The pressurization of the interior space 815 with respect to the ambient atmosphere creates a pressure differential across the semi-permeable material 812. This pressure differential causes the air or other gas to pass (relatively slowly) across the semi-permeable material 812 and into contact with the patient's skin or a material adjacent the patient's skin. The air or gas provided to the patient 900 across the semi-permeable material is intended to control the temperature and humidity at the patient's skin and to help reduce and evaporate perspiration or other moisture.

A controller (for example, controller 400 shown in FIG. 1) may monitor the pressure the in the bladder 810 and provide additional gas to the bladder 810 to account for the gas passing through the semi-permeable material 812. The control system may use a suitable pressure detection mechanism (for example, a pressure sensor) to maintain a desired pressure.

In addition to controlling gas pressure in the bladder 812, the temperature and/or humidity of the gas provided to the bladders 210*a*, 210*b*, 210*c*, 210*d* may be controlled. For example, the gas (e.g., air) may be cooled and dehumidified with respect to ambient air such that the gas passing though the semi-permeable material and into contact with the patient may be better suited to reduce moisture and perspiration and increase patient comfort.

It is believed that the system of FIG. 5 further resists development of pressure sores and increases patient comfort. The humidity and temperature of the air provided to the bladder 810 may be monitored (for example, by temperature and humidity sensors) and controlled accordingly. This monitoring may be performed, for example, at a gas supply source (for example, the pump 820) and/or within the bladder 810. However, the gas may be cooled and/or dehumidified without sensing the temperature and humidity of the gas (for example, to simply the system and control thereof).

As explained above, the system of FIG. 5 may be used with any expandable bladder system described herein, including, for example, the expandable bladders 210*a*, 210*b*, 210*c*, 210*d*, the components as described in the '219 patent, (such as channels 335 and pressure relievers 346 shown in FIG. 1), and/or the vascular compression bladder 510.

Although the present invention has been described with reference to particular examples and exemplary embodiments, the foregoing description is not limiting. Moreover, the apparatus, method, and system described herein may be used in any appropriate combination.

What is claimed is:

1. A therapeutic garment, comprising:
   at least one first expandable bladder configured to underlie a wearer's left shoulder blade;
   at least one second expandable bladder configured to underlie the wearer's right shoulder blade;
   at least one percussive mechanism to transmit ultrasonic waves to the wearer's lungs, wherein the at least one percussive mechanism is disposed in the at least one first expandable bladder and the at least one second bladder; and
   an actuator configured to alternately (a) expand the at least one first expandable bladder from a collapsed state to an expanded state such that the wearer's torso is rolled in a rightward direction and (b) expand the at least one second expandable bladder from a collapsed state to an expanded state such that the wearer's torso is rolled in a leftward direction.

2. The garment according to claim 1, wherein the at least one first expandable bladder is elongated with a longitudinal axis parallel to the wearer's anteroposterior axis, and the at least one second expandable bladder is elongated with a longitudinal axis parallel to the wearer's anteroposterior axis.

3. The garment according to claim 1, wherein the rate of the alternating rolling is adjustable.

4. The garment according to claim 1, wherein said
at least one percussive mechanism further transmits
a direct percussive effect to the wearer's lungs.

5. The garment according to claim 1, further comprising:
at least one vibratory mechanism configured to transmit vibrations to the wearer's lungs.

6. The garment according to claim 5, wherein the at least one vibratory mechanism is disposed in the at least one first expandable bladder and the at least one second expandable bladder.

7. The garment according to claim 1, further comprising:
at least one control panel to set at least one of (a) an intensity of treatment, (b) a duration of treatment, and (c) a frequency of treatment.

8. The garment according to claim 1, further comprising:
at least one sensor to detect at least one of (a) urinary soilage and (b) fecal soilage.

9. The garment according to claim 8, further comprising an alarm that is configured to be triggered by the at least one sensor upon the detection of at least one of (a) urinary soilage and (b) fecal soilage.

10. The garment according to claim 1, further comprising:
at least one third expandable bladder configured to exert a pressure on a vascular access of the wearer that is sufficient to reduce bleeding from the vascular access.

11. The garment according to claim 1, wherein the percussive mechanism is disposed on each the at least one first expandable bladder and the at least one second bladder on a side adjacent the wearer's back configured to improve pulmonary hygiene.

12. A therapeutic garment, comprising:
at least one first expandable bladder configured to underlie a wearer's left shoulder blade;
at least one second expandable bladder configured to underlie the wearer's right shoulder blade;
at least one vibratory and percussive mechanism configured to transmit at least one of (a) ultrasonic waves and (b) a direct percussive effect, to the wearer's lungs, said at least one vibratory and percussive mechanism disposed on the at least one first expandable bladder and the at least one second expandable bladder; and
an actuator configured to alternatingly (a) expand the at least one first expandable bladder from a collapsed state to an expanded state such that the wearer's torso is rolled in a rightward direction and (b) expand the at least one second expandable bladder from a collapsed state to an expanded state such that the wearer's torso is rolled in a leftward direction.

13. The garment according to claim 12, wherein the at least one vibratory and percussive mechanism is a cupping mechanism.

14. The garment according to claim 12, wherein the at least one vibratory and percussive mechanism is a rotating paddle mechanism.

15. The garment according to claim 12, wherein the vibratory and percussive mechanism is disposed on each the at least one first expandable bladder and the at least one second bladder on a side adjacent the wearer's back configured to improve pulmonary hygiene.

\* \* \* \* \*